(12) United States Patent
Tanaka et al.

(10) Patent No.: US 12,319,902 B2
(45) Date of Patent: Jun. 3, 2025

(54) CONTAINER FOR CELL CULTURE AND USE METHOD THEREFOR

(71) Applicant: TOYO SEIKAN GROUP HOLDINGS, LTD., Tokyo (JP)

(72) Inventors: Satoshi Tanaka, Yokohama (JP); Takahiko Totani, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 891 days.

(21) Appl. No.: 16/094,406

(22) PCT Filed: Apr. 14, 2017

(86) PCT No.: PCT/JP2017/015248
§ 371 (c)(1),
(2) Date: Oct. 17, 2018

(87) PCT Pub. No.: WO2017/183570
PCT Pub. Date: Oct. 26, 2017

(65) Prior Publication Data
US 2019/0127677 A1    May 2, 2019

(30) Foreign Application Priority Data
Apr. 18, 2016 (JP) ................ 2016-083193

(51) Int. Cl.
*C12M 1/00* (2006.01)
*C12M 1/28* (2006.01)
(Continued)

(52) U.S. Cl.
CPC ............. *C12M 23/34* (2013.01); *C12M 1/00* (2013.01); *C12M 1/28* (2013.01); *C12M 3/00* (2013.01);
(Continued)

(58) Field of Classification Search
None
See application file for complete search history.

(56) References Cited

U.S. PATENT DOCUMENTS

| | | | |
|---|---|---|---|
| 6,210,959 B1 | 4/2001 | Lodri et al. | |
| 8,551,771 B2 | 10/2013 | Wu et al. | |

(Continued)

FOREIGN PATENT DOCUMENTS

| | | |
|---|---|---|
| CN | 101790683 A | 7/2010 |
| CN | 203625353 U | 6/2014 |

(Continued)

OTHER PUBLICATIONS

International Search Report, issued by International Searching Authority in corresponding International Application No. PCT/JP2017/015248, on Jul. 4, 2017.
(Continued)

*Primary Examiner* — Erin M. Bowers
(74) *Attorney, Agent, or Firm* — Sughrue Mion, PLLC (57) ABSTRACT

Provided is a container for cell culture, provided with a container main body and injection/discharge ports, in which an inside of the container main body is divided into a plurality of cisterns 1st and 2nd by a filter member. Thus, various operations performed upon the cell culture can be simply and efficiently performed.

3 Claims, 7 Drawing Sheets

(51) Int. Cl.
  *C12M 3/00* (2006.01)
  *C12M 3/06* (2006.01)
  *C12M 3/08* (2006.01)
  *C12N 1/00* (2006.01)

(52) U.S. Cl.
  CPC ............... *C12M 3/06* (2013.01); *C12M 3/08* (2013.01); *C12M 29/04* (2013.01); *C12N 1/00* (2013.01)

(56) References Cited

U.S. PATENT DOCUMENTS

| | | | |
|---|---|---|---|
| 2008/0145925 | A1 | 6/2008 | Sakai et al. |
| 2009/0037031 | A1 | 2/2009 | George et al. |
| 2009/0068696 | A1 | 3/2009 | Frimodt-Moller |
| 2010/0028992 | A1 | 2/2010 | Wang et al. |
| 2010/0273262 | A1 | 10/2010 | Wu et al. |
| 2010/0311158 | A1 | 12/2010 | Kang et al. |
| 2011/0020922 | A1* | 1/2011 | Wuenn ............... C12M 29/04 435/297.1 |
| 2014/0335608 | A1 | 11/2014 | Tanaka et al. |
| 2015/0079584 | A1* | 3/2015 | Gevaert ............... C12N 5/0062 435/6.1 |
| 2015/0219622 | A1 | 8/2015 | Hickman |
| 2016/0060588 | A1 | 3/2016 | Nakatsuji et al. |
| 2017/0051241 | A1 | 2/2017 | Obi et al. |

FOREIGN PATENT DOCUMENTS

| | | | |
|---|---|---|---|
| EP | 0 112 155 | A2 | 6/1984 |
| EP | 0 363 262 | A1 | 4/1990 |
| EP | 0402272 | A2 | 12/1990 |
| JP | 59-175877 | A | 10/1984 |
| JP | 3-10674 | A | 1/1991 |
| JP | 2000-93159 | A | 4/2000 |
| JP | 2003-274923 | A | 9/2003 |
| JP | 2008-073048 | A | 4/2008 |
| JP | 2010-63404 | A | 3/2010 |
| JP | 2010-158214 | A | 7/2010 |
| JP | 4605734 | B2 | 1/2011 |
| JP | 2011-244713 | * | 12/2011 |
| JP | 2011-244713 | A | 12/2011 |
| JP | 5536642 | B2 | 7/2014 |
| JP | 2014-233209 | A | 12/2014 |
| JP | 5731704 | * | 6/2015 |
| JP | 5731704 | B1 | 6/2015 |
| JP | 2015-522278 | A | 8/2015 |
| JP | 2015-524674 | A | 8/2015 |
| TW | 200740994 | A | 11/2007 |
| TW | 201005090 | A | 2/2010 |
| TW | 201038730 | A1 | 11/2010 |
| WO | 00/78932 | A1 | 12/2000 |
| WO | WO 01/51206 | * | 7/2001 |
| WO | 2008/153401 | A1 | 12/2008 |
| WO | WO 2008/153401 | * | 12/2008 |
| WO | 2013/114845 | A1 | 8/2013 |
| WO | 2014/003640 | A1 | 1/2014 |
| WO | WO 2014/043616 | * | 3/2014 |
| WO | 2014/136581 | A1 | 9/2014 |
| WO | 2015/030639 | A1 | 3/2015 |

OTHER PUBLICATIONS

Written Opinion of the International Searching Authority dated Jul. 4, 2017 in International Application No. PCT/JP2017/015248.
Communication dated Mar. 29, 2021, from the Taiwanese Intellectual Property Office in corresponding application No. 106112942.
Communication issued Nov. 26, 2020 by the Korean Patent Office in application No. 10-2018-7028050.
Machine translation of JP 2014-233209 published Dec. 15, 2014.
Communication dated Nov. 22, 2019, from the European Patent Office in counterpart European Application No. 17785908.9.
Office Action issued Apr. 7, 2021 in Chinese Application No. 201780018246.3.
Zheng et al., "Comparative Study on Various Subpopulations in Mesenchymal Stem Cells of Adult Bone Marrow", Journal of Experimental Hematology, 2005, vol. 13, No. 1, pp. 54-58 (5 pages total).
Notice of Reasons for Refusal dated Sep. 7, 2021 by the Japanese Patent Office in corresponding Japanese Application No. 2018-513155.
Office Action dated Dec. 20, 2022 from the Japanese Patent Office in corresponding JP Application No. 2022-000714.
Office Action issued Jan. 17, 2023 in corresponding Taiwanese patent application No. 110136567.
Office Action issued Mar. 5, 2024 in corresponding Japanese Application No. 2023-024198.
Office Action issued Mar. 5, 2024 in corresponding Japanese Application No. 2023-024199.
Office Action issued Mar. 5, 2024 in corresponding Japanese Application No. 2023-024200.

* cited by examiner

CONTAINER FOR CELL CULTURE AND USE METHOD THEREFOR

CROSS REFERENCE TO RELATED APPLICATIONS

This application is a National Stage of International Application No. PCT/JP2017/015248 filed Apr. 14, 2017, claiming priority based on Japanese Patent Application No. 2016-083193 filed Apr. 18, 2016.

TECHNICAL FIELD

The present invention relates to a container provided for use in the cell culture in order to simply and efficiently perform various operations to be performed in the cell culture, and to a use method therefor.

TECHNICAL BACKGROUND

In recent years, efficient culture and differentiation-induction of a large amount of cells (comprising tissues, microorganisms, viruses, and the like) in an artificial environment have been requested in the production of medicine or in fields such as gene therapy, regenerative medicine, and immunotherapy.

In order to respond to such a requirement, the present applicant has continued studies on a cell culture system capable of efficiently culturing the cell, while a closed-system environment is established to reduce a risk of contamination.

For example, the present applicant proposes a cell culture kit in which a culture container for culturing cells, a culture medium storage container for storing a culture medium or the like, a cell injection container for injecting cells, and a cell collection container for collecting a cell suspension after culturing are connected through a conduit pipe to establish a closed system environment in Patent Literature 1. According to such a cell culture kit, a process from the injection of cells through the addition of a culture medium, the sampling and the collection of the cells can be achieved in a kit while a closed system is maintained.

CITATION LIST

Patent Literature

Patent Literature 1: WO 2013/114845 A

SUMMARY OF INVENTION

Technical Problem

Incidentally, Patent Literature 1 discloses an example in which, upon collecting a cultured cell, a culture container is left to stand to cause precipitation of the cell in a cell suspension, and then a supernatant of the cell suspension is discharged therefrom to reduce a liquid amount, and then a concentrated cell suspension is transferred from the culture container to a cell collection container.

Moreover, cell culture ordinarily requires a period of several days to several weeks. Therefore, when necessary, medium is exchanged during culture so as not to inhibit growth of a cell by exhaustion of a medium component or accumulation of a metabolite of the cell. Upon exchanging the medium, it is considered that an old medium is removed by discharging a supernatant of the cell suspension therefrom, and simultaneously a new medium is added thereto in place thereof.

However, in order to collect the cell or exchange the medium in such a manner, the culture container should be left to stand to precipitate the cell inside the cell suspension prior to discharging the supernatant of the cell suspension therefrom, which requires time until the cell is precipitated. On the other hand, even if the cell in the cell suspension is precipitated by spending sufficient time, the cell is mixed in the supernatant by a discharge operation, and the cell is also liable to be discharged therefrom together with the supernatant. In particular, in exchanging the medium, it is desired that the old medium is removed as much as possible, and a larger amount of the new medium is added thereto. However, accordingly as a discharged amount of the supernatant increases, mixing of the cell is unable to be avoided.

Moreover, in order to prevent the cell from being discharged therefrom together with the old medium upon exchanging the medium, it is also considered that a filter is attached to a flow path of a port provided in the culture container.

However, a diameter of the flow path of the port is ordinarily about 1 to about 10 mm and an area of the filter becomes relatively small, and therefore the filter is easily clogged by a caught cell, and is liable to hinder the discharge of the old medium. Further, the cell caught in the filter is also liable to be dead while being caught in the filter without being returned to the culture container.

The present invention has been made in view of the above-described circumstances, and an objective of the present invention is to provide a container provided for use in the cell culture for simply and efficiently performing various operations to be performed upon the cell culture, in which the cell is suppressed from being discharged therefrom together with the old medium upon exchanging the medium, for example, and a use method therefor.

Solution to Problem

A container according to the present invention, wherein the container for cell culture is provided for use in the cell culture and comprises a container main body and injection/discharge ports, in which an inside of the container main body is divided into a plurality of cisterns by at least one filter member.

Advantageous Effects of Invention

According to the present invention, various operations performed upon cell culture can be simply and efficiently performed.

DESCRIPTION OF EMBODIMENTS

Hereinafter, a preferred embodiment of the present invention will be described with reference to drawings.

First Embodiment

First, a first embodiment of the present invention will be described.

Figure 1:
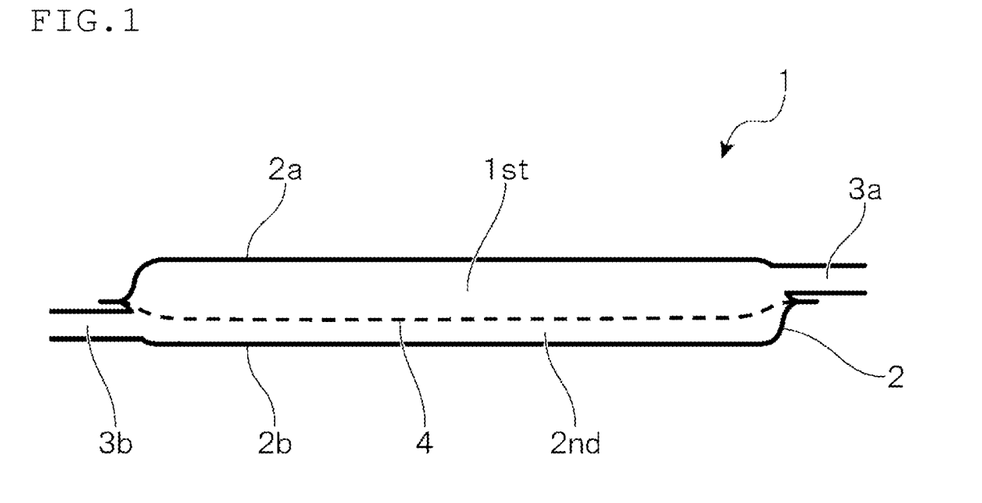
FIG. 1 is an explanatory drawing showing one example of a container for cell culture according to a first embodiment of the present invention.

It should be noted that FIG. 1 is an explanatory drawing showing one example of a container for cell culture according to the present embodiment.

A container 1 shown in FIG. 1 as one example of the present embodiment is provided with a container main body 2 and injection/discharge ports 3a and 3b. Then, an inside of the container main body 2 is divided into a first cistern 1st on a side of a top surface 2a, and a second cistern 2nd on a side of a bottom surface 2b by a sheet-shaped filter member 4. The first cistern 1st on the side of the top surface 2a and the second cistern 2nd on the side of the bottom surface 2b are provided with the injection/discharge ports 3a and 3b, respectively.

With regard to the container main body 2, a specific form thereof is not limited, as long as the container main body 2 can house a culture medium or a cell suspension formed by suspending a cell into a medium without any hindrance to culturing. For example, the container main body 2 may be formed into a container molded in a predetermined shape by injection molding or blow molding, or a pouch-shaped container in which two plastic films are stacked and a peripheral portion is sealed.

The injection/discharge ports 3a and 3b are parts to be an inlet and an outlet upon injecting and discharging the medium or the cell thereinto and therefrom, or the like, and can be provided by attaching a tubular member through which the medium, the cell or the like can be circulated to the container main body 2, for example.

Moreover, although not particularly shown, the container 1 may be configured in such a manner that the first cistern 1st on the side of the top surface 2a and the second cistern 2nd on the side of the bottom surface 2b are further provided with injection/discharge ports for sampling the medium or the cell during the culture, or the like, for example.

Each of the cisterns divided by the filter member 4 can be provided with two or more injection/discharge ports, when necessary.

In one example shown in FIG. 1, the container main body 2 is formed of a plastic film, is sealed at a peripheral portion thereof, has a bulging shape in which the top surface 2a thereof is bulged like a plateau, and is formed so that a rim of the bottom surface 2a formed into a flat surface is inclined and connected to the peripheral portion. Further, the container main body 2 also has the bulging shape in which the bottom surface 2b thereof is bulged like a plateau, and is formed so that a rim of the bottom surface 2b formed into the flat surface is inclined and connected to the peripheral portion.

The container main body 2 has such a bulging shape to allow prevention of deformation upon injecting the medium or the cell thereinto.

More specifically, in a flat pouch-shaped container formed merely by stacking two plastic films and sealing the peripheral portion, the bottom surface is deformed in such a manner that the peripheral portion is lifted up accordingly as the inside of the container is filled with a content liquid. However, by designing the bulging shape of the container main body 2 in considering an injection amount, deformation of the container main body 2 upon injecting the medium or the cell thereinto can be suppressed to keep the bottom surface 2b of the container main body 2 in the flat surface.

Accordingly, the container 1 shown in FIG. 1 is preferably used when it is required that the cell in the medium is uniformly precipitated on the bottom surface 2b of the container main body 2 to avoid occurrence of deviation of density of the cell precipitated on the bottom surface 2b (the number of cells per unit area).

The container 1 shown in FIG. 1 can be manufactured as described below, for example.

First, two plastic films and a sheet-shaped filter member 4 are arranged, and when necessary, cut and uniformized in a size thereof. Then, one of the plastic films is applied as a top surface side plastic film to be on the side of the top surface 2a of the container main body 2, and the other plastic film is applied as a bottom surface side plastic film to be on the side of the bottom surface 2b of the container main body 2, and the plastic films each are formed so as to bulge like a plateau by vacuum forming or pressure forming, with leaving the peripheral portions.

Next, the sheet-shaped filter member 4 is inserted between the thus formed top surface side plastic film and the thus formed bottom surface side plastic film, and the peripheral portions thereof are superposed. Then, tubular members to form the injection/discharge ports 3a and 3b are interposed between the top surface side plastic film and the filter member 4, and between the bottom side plastic film and the filter member 4, in predetermined positions in the peripheral portions, respectively, and the peripheral portions are sealed by thermal fusion bonding in the state, and when necessary, the peripheral portions are trimmed. Thus, the container 1 shown in FIG. 1 is manufactured.

The plastic film for forming the container main body 2 is preferably a material having gas permeability of 5,000 mL/(m$^2$·day·atm) or more in an oxygen permeability rate measured at a test temperature of 37° C. in accordance with gas permeability test method of JIS K 7126.

Moreover, it is preferable that the plastic film partly or entirely has transparency so that the progress of cell culture, the states of cells, and the like can be checked.

A material used for the plastic film that forms the container main body 2 is not particularly limited. For example, the material includes thermoplastic resins such as polyethylene, polypropylene, ethylene-vinyl acetate copolymer, polyester, silicone-based elastomer, polystyrene-based elastomer, and tetrafluoroethylene-hexafluoropropylene copolymer (FEP). These materials may be used in a single layer, or materials of the same kind or different kinds may be used in a laminated layer, but preferably have predetermined gas permeability. Further, in consideration of heat fusion bonding properties during sealing the peripheral portion, it is preferable to have a layer functioning as a sealant layer.

Moreover, in order to have flexibility and yet have moderate shape maintaining properties that maintain the bulging shape of the container main body 2, the thickness of the plastic film used to form the container main body 2 is preferably 30 to 200 μm.

Moreover, the tubular member for forming the injection/discharge ports 3a and 3b can be molded into a predetermined shape by injection molding, extrusion molding or the like by using a thermoplastic resin of polyethylene, polypropylene, vinyl chloride, a polystyrene-based elastomer, FEP or the like, for example.

Moreover, the filter member 4 is formed by using a porous body having pores through which at least passage of the medium is allowed; but such a porous body is improper as the body in which the cell enters into the pore and is unable to get out therefrom. From such a viewpoint, the filter member 4 is preferably formed by using a mesh sheet prepared by knitting a synthetic resin fiber formed of polyolefin, polyester, polyamide such as nylon, a fluorine-based resin such as polytetrafluoroethylene, or the like.

A size of the pore in the filter member 4 can be appropriately selected according to a use form of the container 1. The filter member 4 is preferably subjected to hydrophilization treatment for improving passage performance of the medium, and the cell can also be made difficult to adhere thereon by applying the hydrophilization treatment thereto.

Moreover, the filter member 4 only needs to be formed by using the porous body in which at least part thereof is as described above, as long as the function required according to the use form of the container 1 is not adversely affected. For example, upon manufacturing the container 1 as described above, the filter member 4 is formed by holding a circumference of the porous body with the plastic film cut in a frame shape, or the like. Thus, the thermal fusion bonding between the top surface side plastic film and the bottom surface side plastic film can also be further satisfactorily performed.

Moreover, a size of the container main body 2 is not particularly limited, and is preferably adjusted to 50 to 500 mm in length and 50 to 500 mm in width, for example.

Next, a use example of the container 1 shown in FIG. 1 as one example of the present embodiment will be described.

Use Example 1 of First Embodiment

Figure 2A:
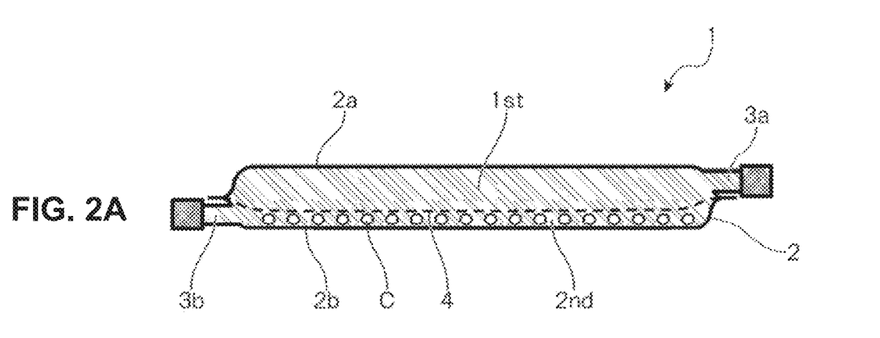
FIGS. 2A to 2C are explanatory drawings showing a use example of the container for cell culture according to the first embodiment of the present invention.
Figure 2B:
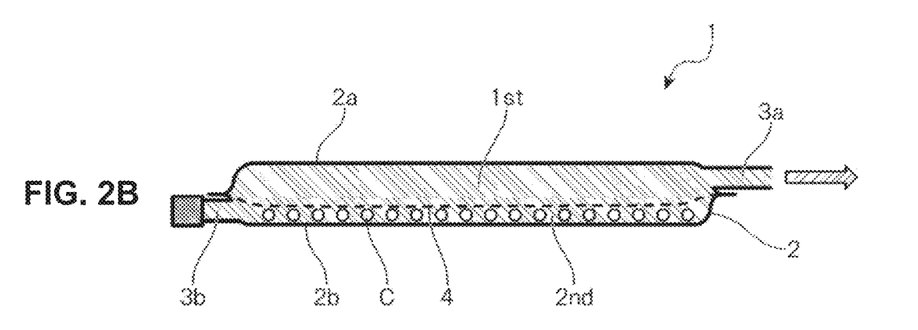
Figure 2C:
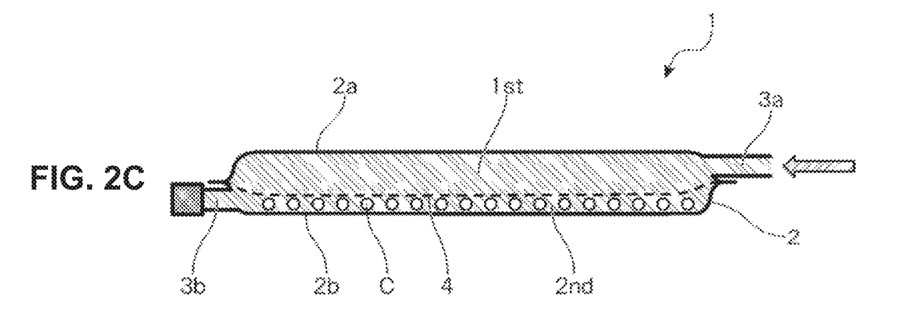

FIGS. 2A to 2C show an example in which the container 1 shown in FIG. 1 is provided for use in cell culture as a culture container in which an operation of exchanging medium or the like can be simply and efficiently performed.

In the present use example, a cell C as a culture object is cultured by being injected into a container main body 2 filled with a medium from an injection/discharge port 3b provided in a second cistern 2nd on a side of a bottom surface 2b. At this case, in considering a size of the cell C as the culture object, as a filter member 4, a member having pores through which passage of such a cell C is not allowed is selected. As a result, the cell C being cultured is retained in the second cistern 2nd on the side of the bottom surface 2b, and cannot move to a first cistern 1st on a side of a top surface 2a (see FIG. 2A).

Upon exchanging the medium during the culture, an old medium is discharged from an injection/discharge port 3a provided in the first cistern 1st on the side of the top surface 2a (see FIG. 2B). At this time, the cell C being cultured can be retained in the second cistern 2nd on the side of the bottom surface 2b, and therefore the cell C is not discharged therefrom together with the old medium, and a larger amount of the old medium can be discharged therefrom. After discharging the old medium therefrom, a new medium in the same amount therewith is injected thereinto from the injection/discharge port 3a provided in the first cistern 1st on the side of the top surface 2a (see FIG. 2C) to continue the culture.

As described above, in the present use example, an operation of exchanging the medium during the culture, in particular, the operation of discharging the old medium therefrom can be simply and efficiently performed.

Moreover, in the container 1 according to the present use example, a content liquid inside the container can be discharged from the injection/discharge port 3a provided in the first cistern 1st on the side of the top surface 2a in a state in which the cell C is retained in the second cistern 2nd on the side of the bottom surface 2b. Therefore, for example, if the container 1 is used as the culture container for the cell culture kit disclosed in Patent Literature 1, an operation of collecting the cell as exemplified in Patent Literature 1 can also be simply and efficiently performed without spending time for precipitation of the cell. Further, the container 1 is used as the cell collection container for the cell culture kit disclosed in Patent Literature 1, and a cell suspension collected from the culture container is transferred to the second cistern 2nd on the side of the bottom surface 2b, and a washing solution is repeatedly injected and discharged into and from the injection/discharge port 3a provided in the first cistern 1st on the side of the top surface 2a, and an operation of washing the cell is performed. Thus, a washing and collection mechanism can be introduced into the cell culture kit in Patent Literature 1.

Moreover, the container 1 can also be applied as an antibody-producing container in such a manner that an antibody-producing cell is cultured in the second cistern 2nd on the side of the bottom surface 2b, and the produced antibody is taken out from the injection/discharge port 3a provided in the first cistern 1st on the side of the top surface 2a.

Thus, in the present use example, as the filter member 4, the member having the pores through which passage of the cell C as the culture object is not allowed is selected, and the cell C is cultured by being injected into one cistern 2nd divided by the filter member 4. Thus, in a state in which the cell C is retained in the cistern 2nd, the medium, the washing solution or the like can be injected and discharged into and from the injection/discharge port 3a provided in the other cistern 1st divided by the filter member 4.

Accordingly, the container 1 may be configured in such a manner that, upon using the container 1 shown in FIG. 1, when necessary, the cell is cultured in the first cistern 1st on the side of the top surface 2a, and the medium, the washing solution or the like is injected and discharged into and from the injection/discharge port 3b provided in the second cistern 2nd on the side of the bottom surface 2b.

Use Example 2 of First Embodiment

Figure 3:
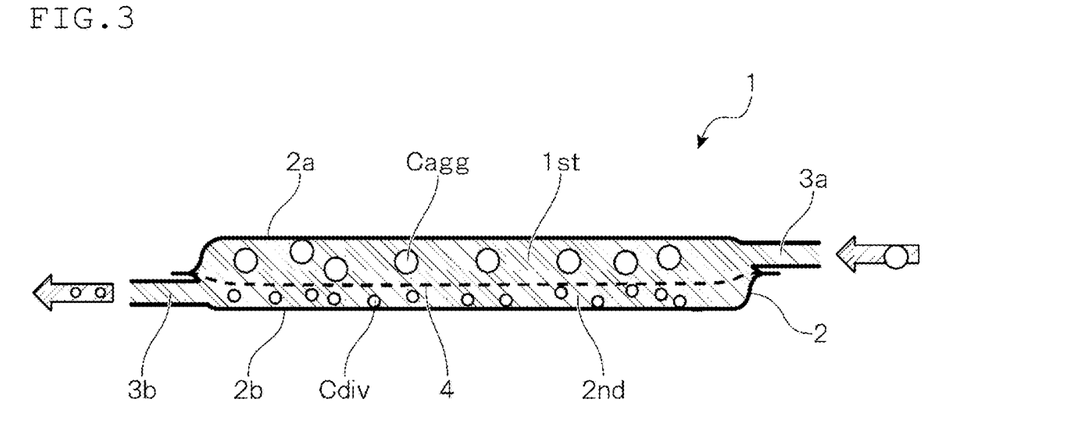
FIG. 3 is an explanatory drawing showing another use example of the container for cell culture according to the first embodiment of the present invention.

FIG. 3 shows an example in which the container 1 shown in FIG. 1 is provided for use in cell culture as an aggregate dividing container in which an operation of dividing an aggregate Cagg of a cell into a desired size can be simply and efficiently performed.

In the present use example, the aggregate Cagg is pumped together with a medium into a container main body 2 filled with a medium from an injection/discharge port 3a provided in a first cistern 1st on a side of a top surface 2a. At this case, as a filter member 4, a member having pores according to a size of the aggregate Cagg desired to be divided is selected. Thus, while the aggregate Cagg is divided into the size according to the size of the pore in the filter member 4, upon passing through the filter member 4, the aggregate Cagg is sent to a second cistern 2nd on a side of a bottom surface 2b.

An aggregate Cdiv divided into the desired size can be taken out from an injection/discharge port 3b provided in the second cistern 2nd on the side of the bottom surface 2b.

Thus, in the present use example, as the filter member 4, the member having the pore according to the size of the aggregate Cagg desired to be divided is selected, and the aggregate Cagg is pumped together with the medium to one cistern 1st divided by the filter member 4. Thus, the operation of dividing the aggregate Cagg into the desired size can be simply and efficiently performed.

Accordingly, the container 1 may be configured in such a manner that, upon using the container 1 shown in FIG. 1, when necessary, the aggregate Cagg is pumped together with the medium from the injection/discharge port 3b provided in the second cistern 2nd on the side of the bottom surface 2b.

Moreover, although not particularly shown, an inside of the container main body 2 is divided into three or more cisterns, and the size of the pore of the filter member 4 for dividing each cistern is appropriately adjusted. Thus, the aggregate Cagg can also be divided stepwise. Further, each cistern is configured to be provided with injection/discharge ports. Thus, the aggregates Cdiv divided into different sizes can be taken out therefrom, respectively.

Use Example 3 of First Embodiment

Figure 4:
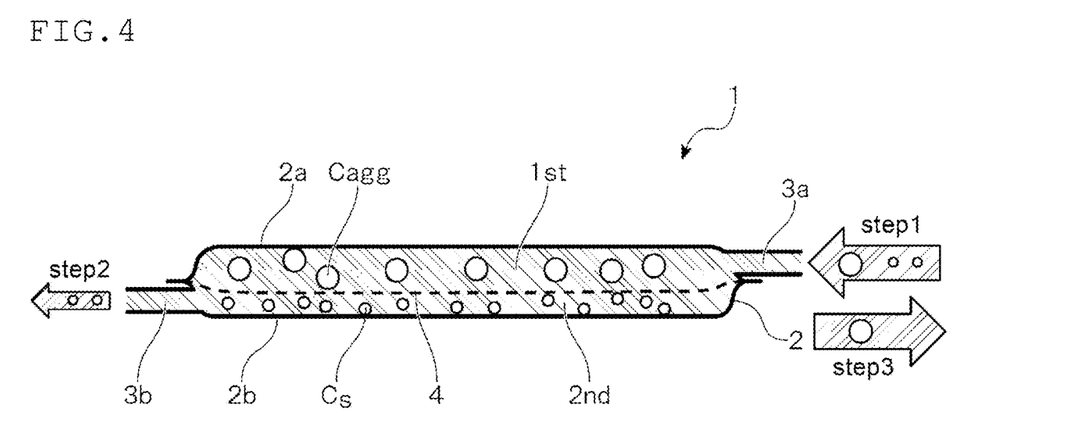
FIG. 4 is an explanatory drawing showing another use example of the container for cell culture according to the first embodiment of the present invention.

FIG. 4 shows an example in which the container 1 shown in FIG. 1 is provided for use in cell culture as a cell separation container in which an operation of separating two kinds of cells having different sizes mixed therein, for example, a single cell Cs and an aggregate Cagg thereof can be simply and efficiently performed.

In the present use example, a cell suspension in which two kinds of cells Cs and Cagg having different sizes mixed therein are injected from an injection/discharge port 3a provided in a first cistern 1st on a side of a top surface 2a into a container main body 2 filled with a medium (step 1). After injection, the container 1 is left to stand, and when necessary vibrated. At this case, as a filter member 4, a member having pores through which, between two kinds of the cells Cs and Cagg desired to be separated, passage of the cell Cs having a smaller size is allowed, but passage of the cell Cagg having a larger size is not allowed is selected. Thus, the container 1 can be configured in such a manner that the cell Cs having the smaller size passes through the pores of the filter member 4, and is precipitated in the second cistern 2nd on the side of the bottom surface 2b, and the cell Cagg having the larger size is retained in the first cistern 1st on the side of the top surface 2a.

The cell Cs having the smaller size precipitated in the second cistern 2nd on the side of the bottom surface 2b is separated from the cell Cagg having the larger size, and can be taken out from an injection/discharge port 3b provided in the second cistern 2nd on the side of the bottom surface 2b (step 2). On the other hand, the cell Cagg having the larger size separated from the cell Cs having the smaller size and retained in the first cistern 1st on the side of the top surface 2a can be taken out from the injection/discharge port 3a provided in the first cistern 1st on the side of the top surface 2a (step 3).

Thus, in the present use example, as the filter member 4, the member having the pores through which passage of at least one cell between the cells mixed therein is allowed, but passage of the cell other than the cell described above is not allowed is selected, and the cells having different sizes mixed therein are injected into one cistern 1st divided by the filter member 4, and the cell passed through the filter member 4 is taken out from the other cistern 2nd divided by the filter member 4. Thus, an operation of separating the cells having different sizes mixed therein can be simply and efficiently performed.

Accordingly, although not particularly shown, the container 1 is configured in such a manner that an inside of the container main body 2 is divided into three or more cisterns, a size of the pore in the filter member 4 for dividing each cistern is appropriately adjusted, and simultaneously each cistern is provided with injection/discharge ports. Thus, three or more kinds of cells having different sizes can also be separated.

Use Example 4 of First Embodiment

Figure 5:
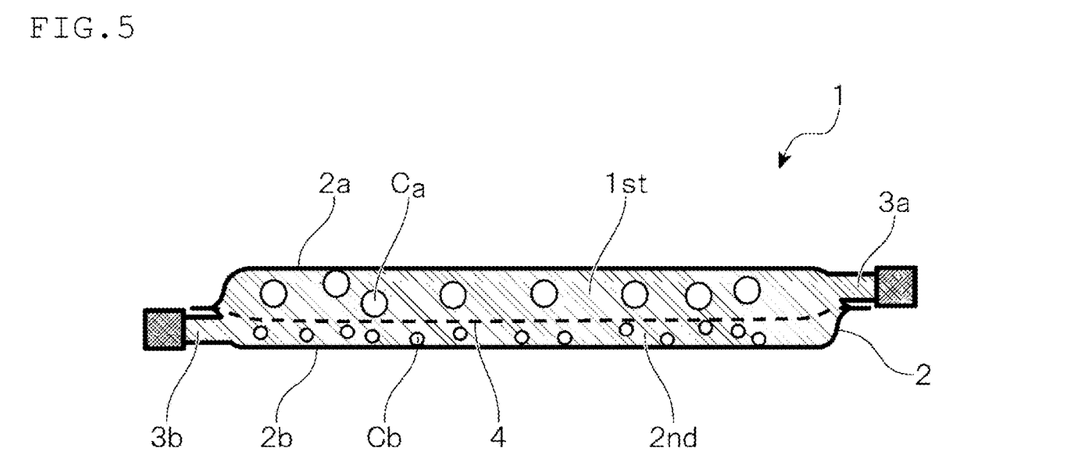
FIG. 5 is an explanatory drawing showing another use example of the container for cell culture according to the first embodiment of the present invention.

FIG. 5 shows an example in which the container 1 shown in FIG. 1 is provided for use in cell culture as a co-culture container in which different kinds of cells Ca and Cb are co-cultured in the same container, and then an operation of separately taking out the cells can be simply and efficiently performed.

In the present example, the cell Ca and the cell Cb are co-cultured by injecting the cell Ca from an injection/discharge port 3a provided in a first cistern 1st on a side of a top surface 2a into a container main body 2 filled with a medium, and simultaneously injecting the cell Cb from an injection/discharge port 3b provided in a second cistern 2nd on a side of a bottom surface 2b thereinto. At this case, as a filter member 4, a member having pores through which passage of any of the cells Ca and Cb is not allowed is selected. Thus, both can be co-cultured within the same container without being mixed therein in a state in which one cell Ca is retained in the first cistern 1st on the side of the top surface 2a and the other cell Cb is retained in the second cistern 2nd on the side of the bottom surface 2b, respectively.

After completion of the culture, one cell Ca can be taken out from the injection/discharge port 3a provided in the first cistern 1st on the side of the top surface 2a, and the other cell Cb can be taken out from the injection/discharge port 3b provided in the second cistern 2nd on the side of the bottom surface 2b.

Thus, in the present use example, as the filter member 4, the member having the pores through which passage of any of the cells Ca and Cb to be co-cultured is not allowed is selected, and different kinds of the cells Ca and Cb are separately injected into respective cisterns 1st and 2nd divided by the filter member 4 for each kind. Thus, the cells Ca and Cb can be co-cultured in the same container without being mixed therein. After completion of the culture, an operation of separately taking out the cells can be simply and efficiently performed.

Accordingly, although not particularly shown, the container 1 is configured in such a manner that an inside of the container main body 2 is divided into three or more cisterns, and each cistern is provided with injection/discharge ports. Thus, three or more kinds of the cells can also be co-cultured.

Second Embodiment

Next, a second embodiment of the present invention will be described.

Figure 6:
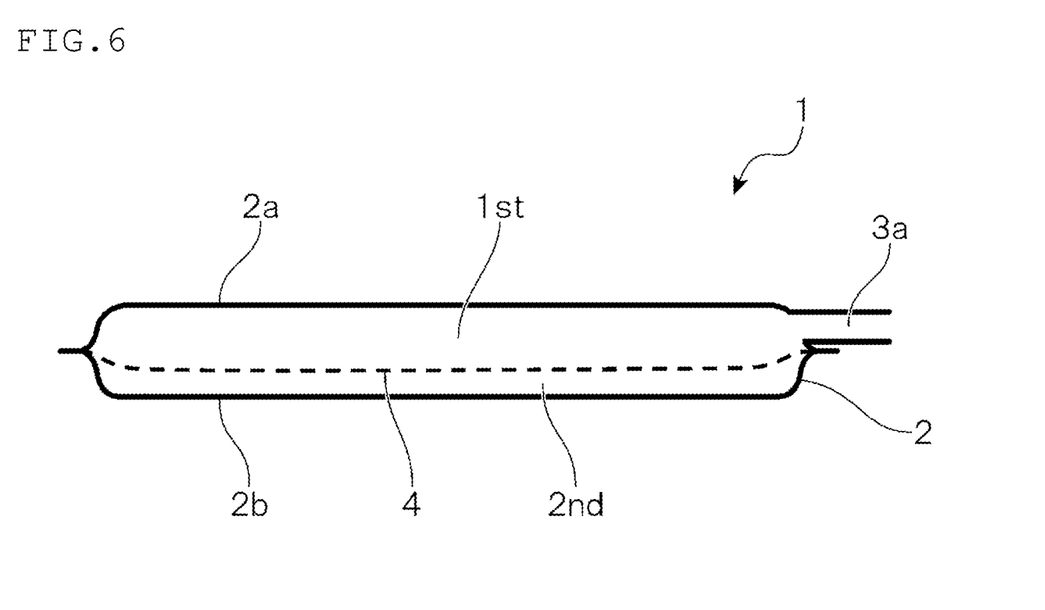
FIG. 6 is an explanatory drawing showing one example of a container for cell culture according to a second embodiment of the present invention.

It should be noted that FIG. 6 is an explanatory drawing showing one example of a container for cell culture according to the present embodiment.

A container 1 shown in FIG. 6 as one example of the present embodiment is provided with a container main body 2 and an injection/discharge port 3a. Then, an inside of the container main body 2 is divided into a first cistern 1st on a side of a top surface 2a and a second cistern 2nd on a side of a bottom surface 2b by a sheet-shaped filter member 4. The first cistern 1st on the side of the top surface 2a is provided with the injection/discharge port 3a.

The container 1 shown in FIG. 6 is different from the container 1 shown in FIG. 1 as one example of the first embodiment in that the second cistern 2nd on the side of the bottom surface 2b is not provided with an injection/discharge port 3b; but a configuration other than the point is common thereto. Such a container 1 can be manufactured in the same manner as the container 1 shown in FIG. 1 of the first embodiment. On the above occasion, a tubular member for forming the injection/discharge port 3b only needs to be omitted.

The present second embodiment is different from the above-described first embodiment in that the second cistern 2nd on the side of the bottom surface 2b is not provided with the injection/discharge port 3b, and the configuration other than the point is common to the configuration in the above-described first embodiment, and therefore the duplicate description will be omitted.

It should be noted that a specific form of the container main body 2 is not obviously limited in the same manner as in the first embodiment.

Next, a use example of the container 1 shown in FIG. 6 will be described as one example of the present embodiment.

Use Example of Second Embodiment

Figure 7A:
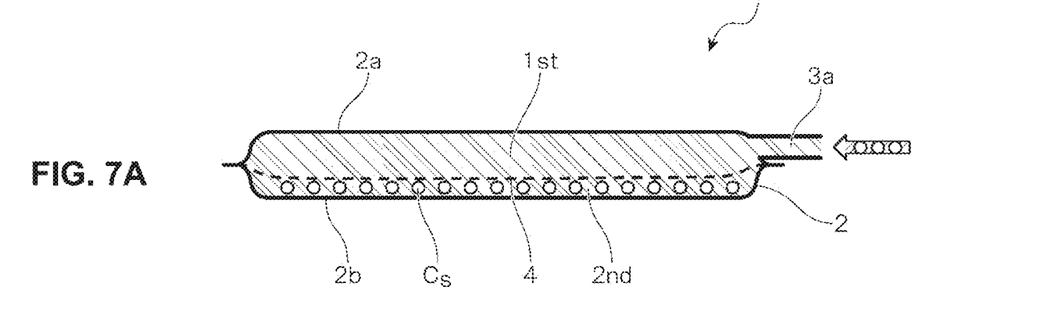
FIGS. 7A to 7C are explanatory drawings showing a use example of the container for cell culture according to the second embodiment of the present invention.
Figure 7B:
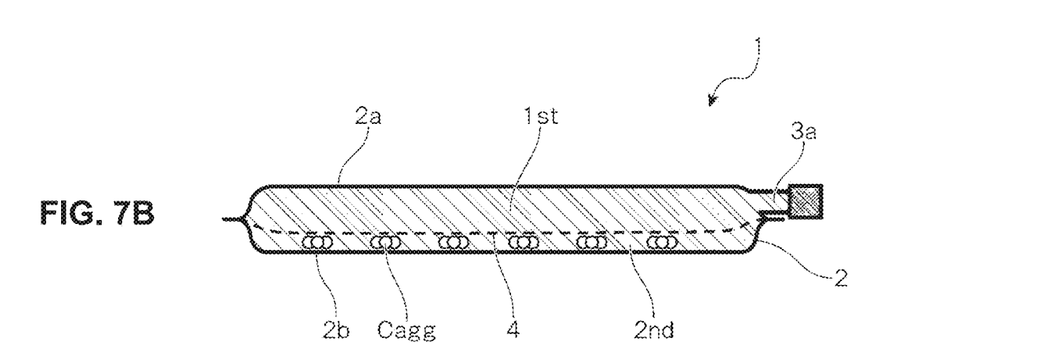
Figure 7C:
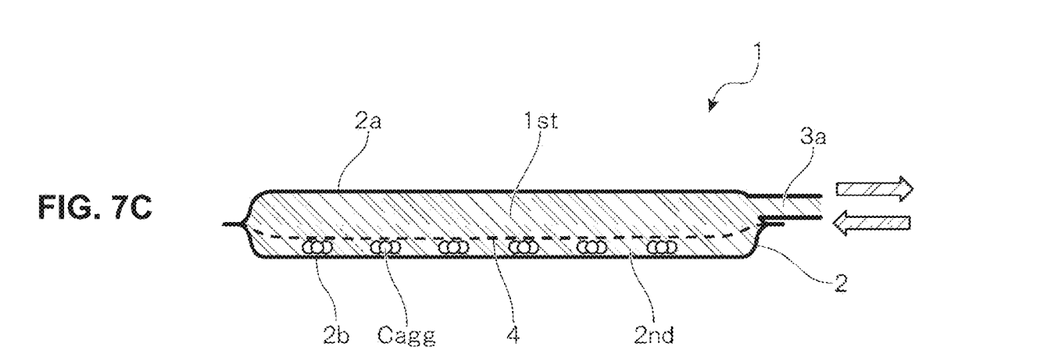

FIGS. 7A to 7C show an example in which the container 1 shown in FIG. 6 is provided for use in cell culture as a culture container in which an operation of exchanging medium or the like can be simply and efficiently performed, in culturing a cell Cs forming an aggregate Cagg.

In the present use example, the cell Cs forming the aggregate Cagg is applied as a culture object, and as a filter member 4, a member having pores through which passage of the cell (single cell) Cs before forming the aggregate Cagg is allowed, but passage of the aggregate Cagg is not allowed is selected.

Thus, if the cell (single cell) Cs as the culture object is injected from an injection/discharge port 3a provided in a first cistern 1st on a side of a top surface 2a into the container main body 2 filled with a medium, the cell Cs passes through the filter member 4, and is precipitated in a second cistern 2nd on a side of a bottom surface 2b FIG. 7A. Then, if the culture progresses, the cell Cs forms the aggregate Cagg, which cannot pass through the filter member 4. Thus, the culture can be progressed in a state in which the aggregate Cagg is retained in the second cistern 2nd on the side of the bottom surface 2b see FIG. 7B.

Accordingly, upon exchanging the medium during the culture, an old medium is discharged from the injection/discharge port 3a provided in the first cistern 1st on the side of the top surface 2a, and simultaneously a new medium is injected thereinto (see FIG. 7C). Thus, the medium can be exchanged in the state in which the aggregate Cagg is retained in the second cistern 2nd on the side of the bottom surface 2b. Further, after completion of the culture, a washing solution is repeatedly injected and discharged into and from the injection/discharge port 3a provided in the first cistern 1st on the side of the top surface 2a. Thus, the aggregate Cagg can also be washed in the state in which the aggregate Cagg is retained in the second cistern 2nd on the side of the bottom surface 2b.

Thus, in the present use example, in culturing the cell Cs forming the aggregate Cagg, as the filter member 4, the member having the pores through which passage of the cell Cs before forming the aggregate Cagg is allowed, but passage of the aggregate Cagg is not allowed is selected. The cell Cs is injected into the first cistern 1st, and then is precipitated in the second cistern 2nd, and the cell is cultured in the state in which the formed aggregate Cagg is retained in the second cistern 2nd. Thus, the operation of exchanging the medium during the culture, washing after completion of the culture, or the like can be simply and efficiently performed.

Then, after washing, the container 1 can also be used for storing and conveying the cultured cell (aggregate Cagg) by injecting a preservation solution or the like into the container main body 2.

It should be noted that, although not particularly shown, if the container 1 is configured in such a manner that the second cistern 2nd on the side of the bottom surface 2b is provided with an injection/discharge port 3b in the same manner as in the first embodiment described above, the cultured cell (aggregate Cagg) can also be taken out from the injection/discharge port 3b.

Third Embodiment

Next, a third embodiment of the present invention will be described.

Figure 8:
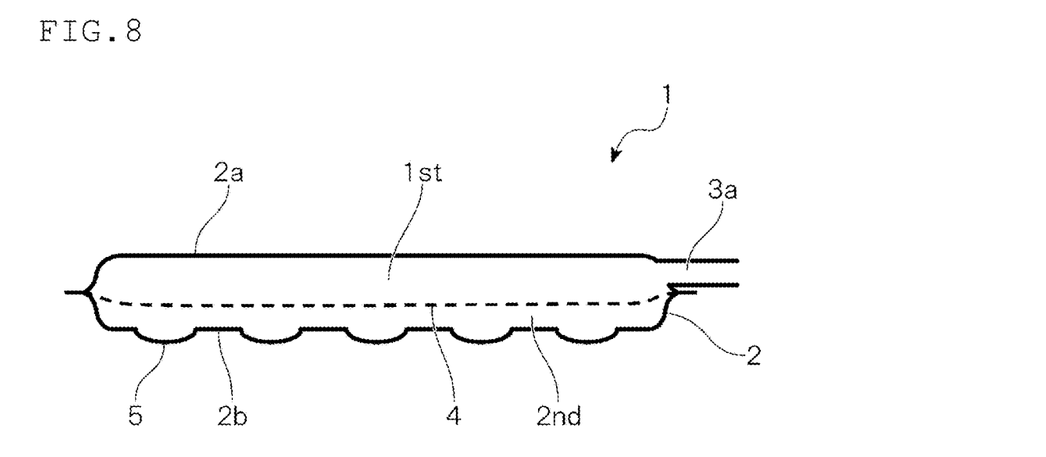
FIG. 8 is an explanatory drawing showing one example of a container for cell culture according to a third embodiment of the present invention.

It should be noted that FIG. 8 is an explanatory diagram showing one example of a container for cell culture according to the present embodiment.

A container 1 shown in FIG. 8 as one example of the present embodiment is provided with a container main body 2 and an injection/discharge port 3a. An inside of the container main body 2 is divided into a first cistern 1st on a side of a top surface 2a and a second cistern 2nd on a side of a bottom surface 2b by a sheet-shaped filter member 4. The first cistern 1st on the side of the top surface 2a is provided with the injection/discharge port 3a, and simultaneously a plurality of concave portions 5 are provided on the bottom surface 2b of the container main body 2.

The container 1 shown in FIG. 8 is different from the container 1 shown in FIG. 6 as one example of the second embodiment in that the plurality of concave portions 5 are provided on the bottom surface 2b of the container main body 2, but a configuration other than the point is common thereto. Such a container 1 can be manufactured in the same manner as the container 1 shown in FIG. 6 of the second embodiment. Upon forming a bottom side plastic film, the concave portions 5 can be formed with a desired shape and alignment by appropriately adjusting a die or the like.

The cell precipitating in a medium is collected in a bottom portion of each concave portion 5 by providing the plurality of concave portions 5 on the bottom surface 2b of the container main body 2, and the cell can be efficiently cultured in a state in which a cell density is increased. In order to configure the container in such a manner that the cell collected in the bottom portion of each concave portion 5 is retained in one concave portion 5 without moving inside the container main body 2, and the state in which the cell density is increased is maintained, an opening size (diameter) in the concave portion 5 is preferably 0.3 to 10 mm, more preferably 0.3 to 5 mm, further preferably 0.5 to 4 mm, and particularly preferably 0.5 to 2 mm, and a depth is preferably 0.1 mm or more.

Moreover, in the example shown in FIG. 8, the concave portion 5 is formed in a bowl shape, but when necessary, can also be formed in a cone shape, a truncated cone shape, or the like.

The present embodiment is different from the second embodiment described above in that the plurality of concave portions 5 are provided on the bottom surface 2b of the container main body 2, and a configuration other than the point is common to the configuration in the second embodiment described above, and therefore the duplicate description will be omitted.

It should be noted that a specific form of the container main body 2 is obviously not particularly limited in the same manner as in the first and second embodiments.

Next, a use example of the container 1 shown in FIG. 8 as one example of the present embodiment will be described.

Use Example of Third Embodiment

Figure 9:
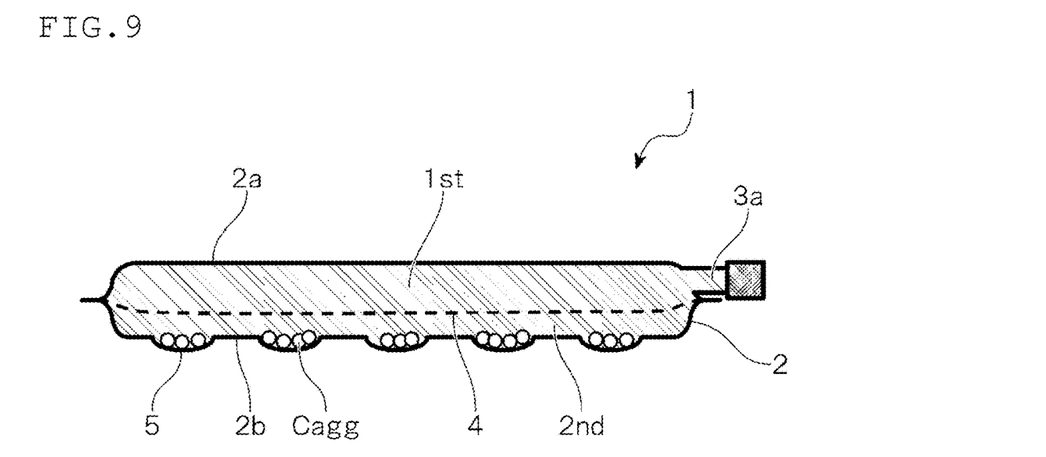
FIG. 9 is an explanatory drawing showing a use example of the container for cell culture according to the third embodiment of the present invention.

FIG. 9 shows one example in which the container 1 shown in FIG. 8 is provided for use in cell culture as a culture container in which, upon culturing a cell Cs forming an aggregate Cagg, the cell Cs is efficiently cultured in a state in which a cell density is increased, and an operation of exchanging medium or the like can be simply and efficiently performed.

In the present use example, the cell Cs forming the aggregate Cagg is applied as a culture object, and as a filter member 4, a member having pores through which passage of the cell (single cell) Cs before forming the aggregate Cagg is allowed, but passage of the aggregate Cagg is not allowed is selected.

Thus, if the cell (single cell) Cs as the culture object is injected from an injection/discharge port 3a provided in a first cistern 1st on a side of a top surface 2a into the container main body 2 filled with the medium, the cell Cs passes through the filter member 4, and is precipitated in a second cistern 2nd on a side of a bottom surface 2b. The precipitated cell Cs is collected in a bottom portion of each portion 5, and can be efficiently cultured in a state in which the cell density is increased. Then, if the culture progresses, the cell Cs forms the aggregate Cagg, which cannot pass through the filter member 4. Thus, the culture can be progressed in a state in which the aggregate Cagg is retained in the second cistern 2nd on the side of the bottom surface 2b.

Accordingly, upon exchanging the medium during the culture, an old medium is discharged from the injection/discharge port 3a provided in the first cistern 1st on the side of the top surface 2a, and simultaneously a new medium is injected thereinto. Thus, while the aggregate Cagg is retained in the second cistern 2nd on the side of the bottom surface 2b, the medium can be exchanged. At this case, although not particularly shown, the filter member 4 is preferably fixed inside the container main body 2 so as to cover an opening portion of the concave portion 5 by adhering the filter member 4 on a circumference of the concave portion 5 (surface positioned between the concave portions 5 adjacent to each other) on the bottom surface 2b, or the like, for example. In such a manner, the cell (aggregate Cagg) can be further reliably retained in one concave portion 5 by inhibiting movement of the cell (aggregate Cagg) collected in the bottom portion of the concave portions 5. Further, after completion of the culture, the aggregate Cagg can be washed by repeatedly injecting and discharging a washing solution into and from the injection/discharge port 3a provided in the first cistern 1st on the side of the top surface 2a, while the aggregate Cagg is retained in the second cistern 2nd on the side of the bottom surface 2b.

Thus, in the present use example, in culturing the cell Cs forming the aggregate Cagg, as the filter member 4, the member having the pores through which passage of the cell Cs before forming the aggregate Cagg is allowed, but passage of the aggregate Cagg is not allowed is selected. The cell Cs is injected into the first cistern 1st, and then is precipitated in the second cistern 2nd, and the precipitated cell Cs is collected in the bottom portion of the concave portion 5. Then, while the cell Cs is efficiently cultured in a state in which the cell density is increased, the cell Cs is cultured in a state in which the formed aggregate Cagg is retained in the second cistern 2nd. Thus, an operation of exchanging the medium during the culture, washing after completion of the culture, or the like can be simply and efficiently performed.

Then, after washing, the container 1 can be used for storing and conveying the cultured cell (aggregate Cagg) by injecting a preservation solution or the like into the container main body 2.

It should be noted that, although not particularly shown, if the container 1 configured in such a manner that the second cistern 2nd on the side of the bottom surface 2b is provided with an injection/discharge port 3b in the same manner as in the first embodiment described above, the cultured cell (aggregate Cagg) can also be taken out from the injection/discharge port 3b.

Fourth Embodiment

Next, a fourth embodiment of the present invention will be described.

Figure 10:
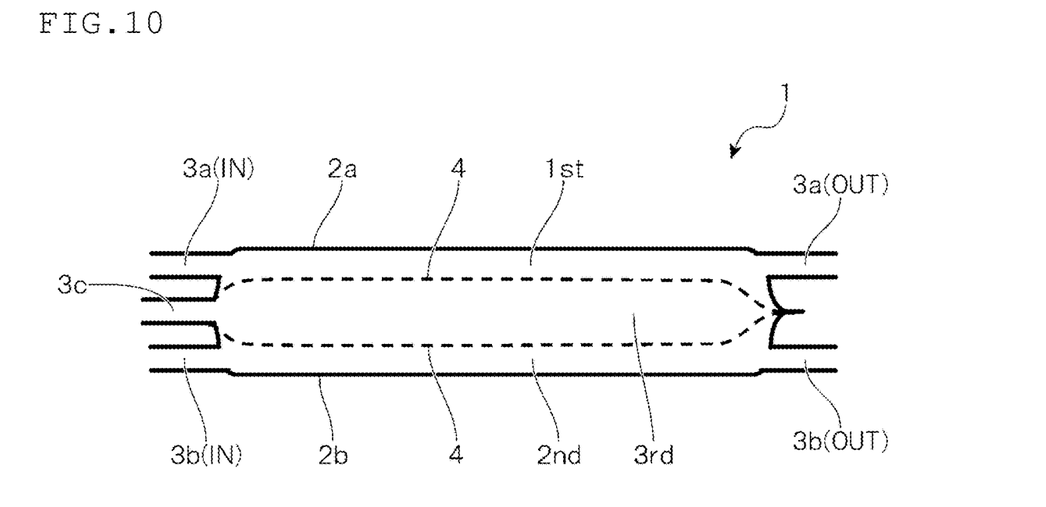
FIG. 10 is an explanatory drawing showing one example of a container for cell culture according to a fourth embodiment of the present invention.

It should be noted that FIG. 10 is an explanatory drawing showing one example of a container for cell culture according to the present embodiment.

A container 1 shown in FIG. 10 as one example of the present embodiment is provided with a container main body 2 and injection/discharge ports 3a, 3b, and 3c. Then, an inside of the container main body 2 is divided into a first cistern 1st on a side of a top surface 2a, a second cistern 2nd on a side of a bottom surface 2b, and a third cistern 3rd positioned therebetween by two sheet-shaped filter members 4.

Moreover, the first cistern 1st on the side of the top surface 2a is provided with injection/discharge ports 3a (IN) and 3a (OUT), serving as an inlet and outlet thereof, and in a manner similar thereto, the second cistern 2nd on the side of the bottom surface 2b is provided with injection/discharge ports 3b (IN) and 3b (OUT), serving as an inlet and outlet thereof. Further, the third cistern 3rd is provided with the injection/discharge port 3c.

The container 1 shown in FIG. 10 is different from the container 1 shown in FIG. 1 as one example of the first embodiment in that the inside of the container main body 2 is divided into three cisterns; each cistern is provided with injection/discharge ports, and simultaneously the first cistern 1st on the side of the top surface 2a is provided with two injection/discharge ports 3a (IN) and 3a (OUT), and the second cistern 2nd on the side of the bottom surface 2b is provided with two injection/discharge ports 3b (IN) and 3b (OUT), but a configuration other than the points is common thereto. Such a container 1 can be manufactured as described below, for example.

First, two plastic films and two sheet-shaped filter members 4 are arranged, and when necessary, cut and uniformized in a size thereof. Then, one plastic film is applied as a top surface side plastic film to be on the side of the top surface 2a of the container main body 2, and the other plastic film is applied as a bottom side plastic film to be on the side of the bottom surface 2b of the container main body 2. The films each are formed so as to bulge like a plateau by vacuum forming or pressure forming, with leaving a peripheral portion thereof.

Next, two sheet-shaped filter members 4 are inserted between the thus formed top surface side plastic film and the thus formed bottom surface side plastic film, and the peripheral portions are superposed. Then, a tubular member for forming the injection/discharge ports 3a (IN) and 3a (OUT) is interposed between the top surface side plastic film and the filter member 4 in a predetermined position of the peripheral portion, a tubular member for forming the injection/discharge ports 3b (IN) and 3b (OUT) is interposed between the bottom surface side plastic film and the filter member 4 in a predetermined position of the peripheral portion, and a tubular member for forming the injection/discharge port 3c is interposed between the two sheet-shaped filter members 4 in a predetermined position of the peripheral portion, and the peripheral portions are sealed by thermal fusion bonding in the state, and when necessary, are trimmed. Thus, the container 1 shown in FIG. 10 is manufactured.

The present embodiment is different from the first embodiment in that the inside of the container main body 2 is divided into three cisterns, and each cistern is provided with injection/discharge ports, and simultaneously the first cistern 1st on the side of the top surface 2a is provided with two injection/discharge ports 3a (IN) and 3a (OUT), and the second cistern 2nd on the side of the bottom surface 2b is provided with two injection/discharge ports 3b (IN) and 3b (OUT), but a configuration other than the points is common to the configuration in the above-described first embodiment, and therefore the duplicate description will be omitted.

It should be noted that a specific form of the container main body 2 is obviously not particularly limited in the same manner as in the first, second, and third embodiments.

Next, a use example of the container 1 shown in FIG. 10 as one example of the present embodiment will be described.

Use Example of Fourth Embodiment

Figure 11:
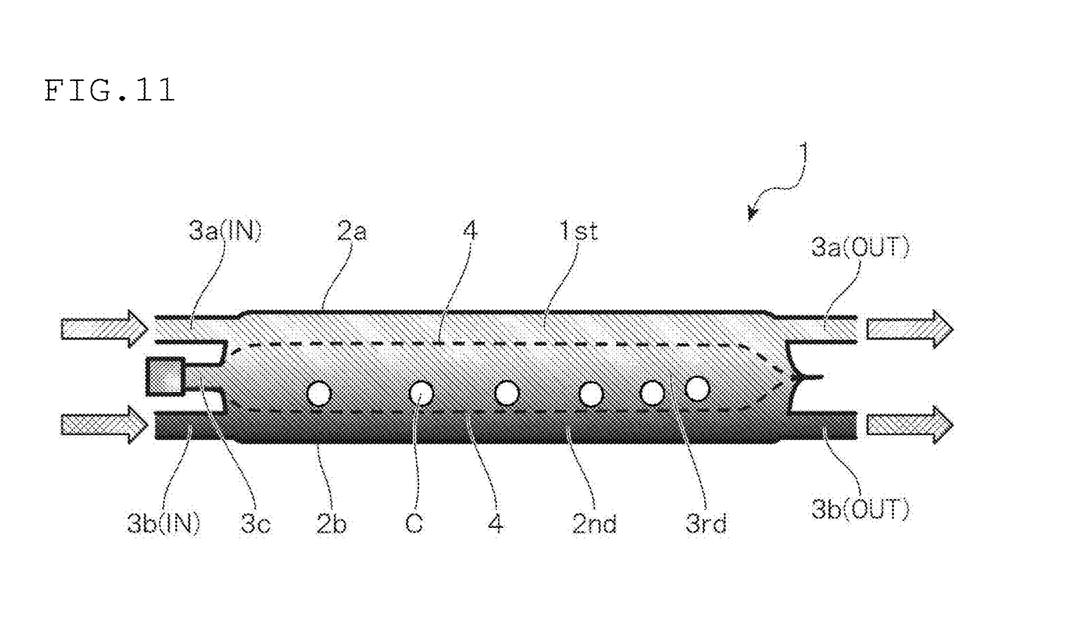
FIG. 11 is an explanatory drawing showing a use example of the container for cell culture according to the fourth embodiment of the present invention.

FIG. 11 shows an example in which the container 1 shown in FIG. 10 is provided for use in cell culture as a culture container in which an operation of reproducing an environment in which a cell C as a culture object is grown, proliferated, or differentiated in vivo can be simply and efficiently performed.

In the present use example, the cell C as the culture object is cultured by injecting the cell C from an injection/discharge port 3c provided in a third cistern 3rd. On the above occasion, media having different component compositions are circulated into a first cistern 1st on a side of a top surface 2a and a second cistern 2nd on a side of a bottom surface 2b, respectively. More specifically, the container 1 is configured in such a manner that the media having different component compositions influent from each of an injection/discharge port 3a (IN) provided in the first cistern 1st on the side of the top surface 2a and an injection/discharge port 3b (IN) provided in the second cistern 2nd on the side of the bottom surface 2b flow out from each of the injection/discharge ports 3a (OUT) and 3b (OUT), while being mixed in the third cistern 3rd.

At this case, in considering a size of the cell C as the culture object, as a filter member 4, a member having pores through which passage of the cell C is not allowed is selected. Then, a medium to be circulated into each of the first cistern 1st on the side of the top surface 2a and the second cistern 2nd on the side of the bottom surface 2b contains various extracellular matrices for controlling growth, proliferation, or differentiation of a cell, or various signal materials for stimulating the cell, or the like. An component composition, an flow amount, a flow rate and the like are adjusted in such a manner that when the materials are mixed in the third cistern 3rd, a concentration gradient, an arrival direction, or the like becomes equivalent to an environment in vivo. Thus, while the environment in vivo is reproduced in the third cistern 3rd, the cell C can be cultured in a state in which the cell C is retained in the third cistern 3rd.

Thus, in the present use example, as the filter member 4, the member having the pores through which passage of the cell C as the culture object is not allowed is selected, and while the media having different component compositions are circulated into each of the first cistern 1st and the second cistern 2nd, the cell C is cultured by injecting the cell C into the third cistern 3rd. Thus, an operation of reproducing the environment in which the cell C as the culture object is grown, proliferated, or differentiated in vivo can be simply and efficiently performed.

Fifth Embodiment

Next, a fifth embodiment of the present invention will be described.

Figure 12:
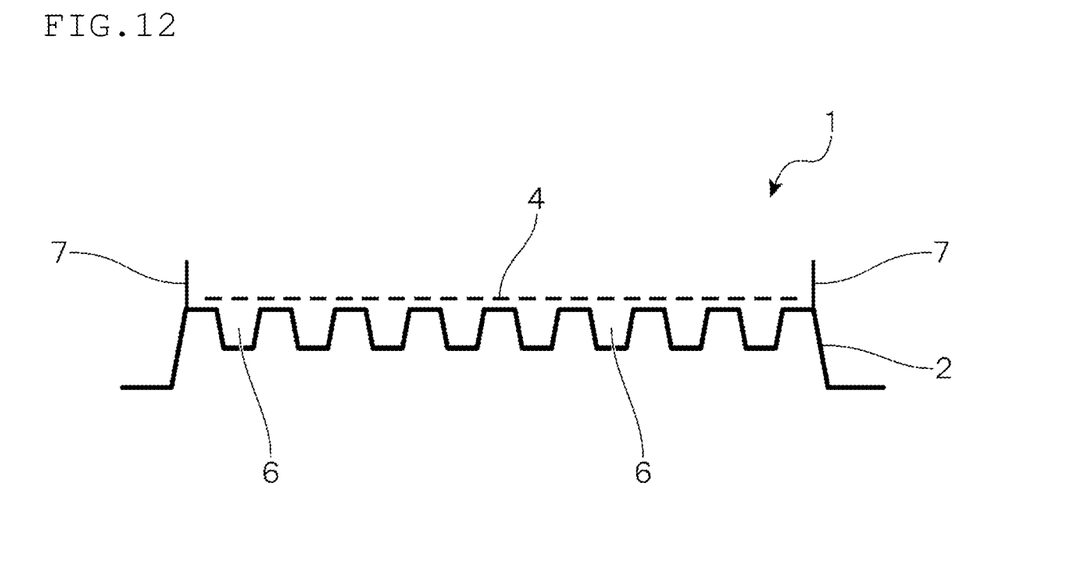
FIG. 12 is an explanatory drawing showing one example of a container for cell culture according to a fifth embodiment of the present invention.

It should be noted that FIG. 12 is an explanatory drawing showing one example of a container for cell culture according to the present embodiment.

A well plate has been widely used so far upon the cell culture. For example, upon differentiation induction from an ES cell or iPS cell to a neural stem cell, cardiac muscle, pancreas, liver, cartilage, or the like, such a method is generally employed, in which a cell is inseminated into the well plate (for example, 96 well plate) to form an aggregate in a well, thereby advancing the differentiation induction.

However, upon culturing the cell by using the well plate, medium should be exchanged for each well. Therefore, complicated pipetting needs to be repeated a number of times by the number of wells in such a manner that an old medium is sucked up with a pipette by taking care not to cause mixing of the cell under culture and discharged therefrom, and subsequently a new medium is injected thereinto with the pipette.

The present embodiment is provided so that an operation of exchanging the medium or the like can be simply and efficiently performed, upon culturing the cell by using a container having a plurality of cell culture portions as the well plate.

A container 1 shown in FIG. 12 as one example of the present embodiment is provided with a container main body 2 having a plurality of concave portions 6 each serving as the cell culture portion, in which an opening portion of each concave portion 6 is covered with a sheet-shaped filter member 4. The filter member 4 covering the opening portion of each concave portion 6 is attached to the container main body 2 so as to closely contact with a circumference of the concave portion 6 (surface positioned between the opening portions of the concave portions 6 adjacent to each other). The filter member 4 is preferably attached to the container main body 2 so as to be peelable.

In the present embodiment, a specific form of the container main body 2 is not particularly limited, as long as the container main body 2 can house the cell or the medium in each concave portion 6 without any hindrance, and the container main body 2 is preferably provided with a side wall portion 7 which rises so as to surround a circumference of the container main body 2.

Moreover, the filter member 4 is as described in the first embodiment described above. In the present embodiment, the cell forming the aggregate is applied as the culture object, and as the filter member 4, a member having pores through which passage of the aggregate is not allowed is selected.

In order to culture the cell as the culture object by using such a container 1, the cell as the culture object is injected, together with the medium, into each concave portion 6 serving as the cell culture portion to start the culture. Then, accordingly as the culture progresses, the cell injected into the concave portion 6 forms the aggregate.

If the culture progresses to arrive at timing of exchanging the medium, the old medium is discharged from each concave portion 6. At this time, the filter member 4 covering the opening portion of each concave portion 6 does not allow passage of the aggregate, and therefore upon exchanging the medium, the old medium only can be flown out by only tipping the container 1, and the old medium can be discharged from each concave portion 6 without accompanying pipetting.

Further, if the side wall portion 7 which rises so as to surround the circumference of the container main body 2 is provided, the new medium is flown into each concave portion 6 only by pouring the new medium inside the side wall portion 7. In this manner, the new medium can be injected into each concave portion 6 without accompanying pipetting.

Then, after completion of the culture, the aggregate can be taken out without being broken up by removing the filter member 4 from the container main body 2, and opening the opening portion of the concave portion 6.

It should be noted that, after completion of the culture, the aggregate can also be washed by injecting and discharging a washing solution into and from each concave portion 6 in the same manner as in exchanging the medium.

Thus, according to the present embodiment, upon culturing the cell forming the aggregate, the operation of exchanging the medium or the like during the culture can be simply and efficiently performed.

As described above, the present invention is described by showing preferred embodiments, but the present invention is obviously not limited to the embodiments described above, and various modifications can be obviously made within the scope of the present invention.

According to the present invention, various operations performed in the cell culture, particularly culture of a sphere (aggregate) formed in a process of subculture of the ES cell or the iPS cell, and differentiation induction from a stem cell thereof to the neural stem cell, the cardiac muscle, the pancreas, the liver, the cartilage, or the like, can be simply and efficiently performed. Moreover, various operations also related to culture of the antibody-producing cell such as a lymphocyte and a hybridoma, and a floating cell such as a megakaryocyte and erythrocyte can be simply and efficiently performed.

The entire contents of Literature described in the description and the description of the Japanese application serving as a basis of claiming the priority concerning the present application to the Paris Convention are incorporated by reference herein.

INDUSTRIAL APPLICABILITY

The present invention can be used as a technology on efficiently culturing a cell in fields of medical and pharmaceutical science and biochemistry.

REFERENCE SIGNS LIST

1 Container (container for cell culture)
2 Container main body
2a Top surface
2b Bottom surface
3a, 3b, 3c injection/discharge port
4 Filter member
5 Concave portion
6 Concave portion
7 Side wall portion
1st First cistern
2nd Second cistern
3rd Third cistern

The invention claimed is:
1. A container for cell culture provided for use in the cell culture, the container comprising:
  a container main body in which two plastic films are stacked and a peripheral portion thereof is sealed to form a pouch-shape container main body; and
  at least one injection/discharge port attached to the container main body at the peripheral portion thereof, wherein
  an inside of the container main body is divided into a first cistern on a side of a top surface of the container main body and a second cistern on a side of a bottom surface of the container main body by a filter member having pores through which passage of the cell before forming an aggregate is allowed, but passage of the aggregate is not allowed;
  at least one of the first cistern on the side of the top surface and the second cistern on the side of the bottom surface is provided with at least one injection/discharge port;
  a plurality of concave portions is provided on the bottom surface of the second cistern of the container main body such that the cells are collected in the bottom portion of each concave portion, and the cells are cultured in the state in which a cell density is increased;

the thickness of each of the plastic films is 30 to 200 μm and each of the plastic films has flexibility; and each of the plastic films for forming the container main body is a material having gas permeability of 5,000 mL/(m²·day·atm) or more in an oxygen permeability rate measured at a test temperature of 37° C., and the container main body is filled with medium when culturing cells.

2. The container for cell culture according to claim 1, wherein the filter member is a mesh sheet prepared by knitting a synthetic resin fiber.

3. The container for cell culture according to claim 1, wherein each concave portions are formed in a bowl shape, a cone shape or a truncated cone shape.

* * * * *